United States Patent [19]

Wu

[11] Patent Number: 4,840,903

[45] Date of Patent: Jun. 20, 1989

[54] PROCESS FOR PRODUCING ETHANOL FROM PLANT BIOMASS USING THE FUNGUS PAECILOMYCES SP.

[75] Inventor: Jung Fu Wu, Lakewood, Colo.

[73] Assignee: The United States of America as represented by the United States Department of Energy, Washington, D.C.

[21] Appl. No.: 763,585

[22] Filed: Aug. 8, 1985

[51] Int. Cl.$^4$ .............................. C12P 7/10; C12R 1/79
[52] U.S. Cl. .................................... 435/165; 435/161; 435/163; 435/932
[58] Field of Search ................ 435/161, 163, 932, 165

[56] References Cited

U.S. PATENT DOCUMENTS

| | | | |
|---|---|---|---|
| 4,282,327 | 8/1981 | Hanka et al. | 435/932 |
| 4,359,534 | 11/1982 | Kurtzman et al. | 435/161 |
| 4,472,501 | 9/1984 | Takasawa et al. | 435/161 |
| 4,477,569 | 10/1984 | Schneider et al. | 435/161 |
| 4,511,656 | 4/1985 | Gong | 435/161 |
| 4,567,145 | 1/1986 | Faber et al. | 435/161 |

*Primary Examiner*—Charles F. Warren
*Attorney, Agent, or Firm*—Kenneth Richardson; James W. Weinberger; Judson R. Hightower

[57] ABSTRACT

A process for producing ethanol from plant biomass is disclosed. The process in cludes forming a substrate from the biomass with the substrate including hydrolysates of cellulose and hemicellulose. A species of the fungus *Paecilomyces*, which has the ability to ferment both cellobiose and xylose to ethanol, is then selected and isolated. The substrate is inoculated with this fungus, and the inoculated substrate is then fermented under conditions favorable for cell viability and conversion of hydrolysates to ethanol. Finally, ethanol is recovered from the fermented substrate.

27 Claims, 3 Drawing Sheets

PROCESS FOR PRODUCING ETHANOL FROM PLANT BIOMASS USING THE FUNGUS PAECILOMYCES SP.

CONTRACTUAL ORIGIN OF THE INVENTION

The United States Government has rights in this invention under Contract No. DE-AC02-83CH10093 between the U.S. Department of Energy and the Solar Energy Research Institute, a Division of Midwest Research Institute.

BACKGROUND OF THE INVENTION

1. Field of the Invention

This invention relates to the production of ethanol and, more particularly, to a process for producing ethanol by the fermentation of plant biomass material. Specifically, the present invention relates to a process for producing ethanol by the fermentation of cellulose and hemicellulose hydrolysates using the fungus *Paecilomyces sp.*

2. Description of the Prior Art is of great interest to a wide variety of industries. In particular, due to past and potential future energy crisis situations, the conversion of such biomass materials to useful fuels such as ethanol is of special interest.

Cellulose and hemicellulose are the two most abundant and renewable raw organic compounds in the world. Together, they compose at least 70 percent of the entire world's plant biomass on a dry weight basis. These raw materials are widely available in the waste from agricultural, forest, vegetable, and food process sources. The efficient recycling of these wastes to useful products, and in particular to fuel such as ethanol, would help to substantially reduce disposal problems as well as to provide an abundant and cheap source of fuel. More specifically, plant biomass generally contains from 40-60 percent cellulose and 30-40 percent hemicellulose, with the balance being lignin. If a process for converting the bulk of the cellulose and hemicellulose to ethanol in high yields could be devised, such a process could provide almost an unlimited supply of fuel.

Generally, cellulose is readily broken down to its glucose and cellobiose hydrolysate by-products by acid hydrolysis or enzymatic hydrolysis treatment. While glucose is readily fermentable by many microorganisms to ethanol, cellobiose has proven difficult, at best, to convert to ethanol. Even then, it is convertible to ethanol only in very low yields. (R. Dekker, *Biotechnology Letters*, Volume 4, No. 7, Pages 411-416, 1982; R. Maleszka, et al., *Biotechnology Letters*, Volume 4, No. 2, pp. 133-136, 1982.)

Hemicellulose is likewise readily converted to its various hydrolysate by-products by mild acid hydrolysis or enzymatic hydrolysis treatment. The resultant by-products include various pentoses (xylose and arabinose being the main derivatives), hexoses (mannose and galactose), and sugar acids. By and far, D-xylose is the major hemicellulose hydrolysate constituting approximately 60 percent of the total hydrolysates produced therefrom.

A variety of processes which use different yeasts to ferment xylose to ethanol have been investigated and disclosed in the literature. A prime motivating force behind these investigations is that the fermentation of 5-carbon sugars derived from hemicellulose is extremely important in order to fully utilize biomass material in producing ethanol. Examples of such prior art techniques include U.S. Pat. Nos. 4,511,656, 4,368,268, 4,359,534, and 4,477,569. Unfortunately, these processes do not convert D-xylose to ethanol in sufficient yields and at sufficiently high rates to be efficient and cost effective.

The utilization of plant biomass will require the effective fermentation of all the sugars derived from the hydrolysate by-products of cellulose and hemicellulose. To date, several bacteria yeasts and fungi have been found to be capable of fermenting various pentoses, hexoses, and D-cellobiose derived from lignocellulosic materials. As previously indicated, however, the end-product ethanol concentrations were quite low with respect to typical glucose fermentations. Possible reasons for such low yields of ethanol are that the microorganisms utilized in such prior fermentation processes cannot tolerate high concentrations of xylose, that microorganism activity is possibly inhibited by high ethanol end-product levels, or that the microorganisms used in these prior processes cannot effectively ferment other minor components of hydrolysates including D-galactose, L-arabinose, D-ribose and/or starch. Other possible reasons for low ethanol yields are that the microorganisms used in these processes produce an appreciable quantity of metabolic by-products such as xylitol and arabitol, or that they cannot efficiently ferment both D-cellobiose and D-xylose.

If a microorganism had the ability to ferment both D-cellobiose and D-xylose, it would enable the process of simultaneous saccharification and fermentation of both cellulose and hemicellulose plant biomass to occur. The only process presently known which makes any reasonable attempt at fermenting both of these substances is the process disclosed in U.S. Pat. No. 4,472,501, wherein the microorganisms *Kluveromyces cellobioborus* or *Kloeckera apiculata* are used. Unfortunately, only low yields of ethanol are obtained utilizing low concentrations of glucose, xylose, and cellobiose. Thus, if effective and efficient bioconversion of plant biomass is to become a reality, a need still exists for a process which efficiently produces high yields of ethanol from mixtures of cellulosic and hemicellulosic materials at high concentrations.

SUMMARY OF THE INVENTION

Accordingly, it is one object of the present invention to provide a process for producing ethanol from plant biomass material.

It is another object of the present invention to provide a process for fermenting hydrolysate compositions derived from cellulose and hemicellulose using a microorganism.

It is yet another object of the present invention to provide a fermentation process for converting xylose, cellobiose, and mixtures thereof to ethanol in high yields.

A further object of the present invention is to provide a process for producing ethanol from starch.

Still another object of the invention is to provide a process for fermenting mixtures of various sugar compositions, including five-carbon and six carbon sugars, to ethanol.

To achieve the foregoing and other objects and in accordance with the purpose of the present invention, a process is provided for producing ethanol from plant biomass. The process includes forming a substrate from the biomass with the substrate including hydrolysates of cellulose and hemicellulose. A species of the fungus Paecilomyces which has the ability to ferment both cellobiose and xylose to ethanol is selected and isolated, and the substrate is then inoculated with this fungus. The inoculated solution is fermented under conditions favorable for cell viability and conversion of hydrolysates to ethanol, and the ethanol is recovered from the fermented solution.

BRIEF DESCRIPTION OF THE DRAWINGS

The accompanying drawings, which are incorporated in and form a part of the specification, illustrate preferred embodiments of the present invention, and together with the description, serve to explain the principles of the invention.

In the drawings.

DETAILED DESCRIPTION OF THE PREFERRED EMBODIMENTS

Figure 1:
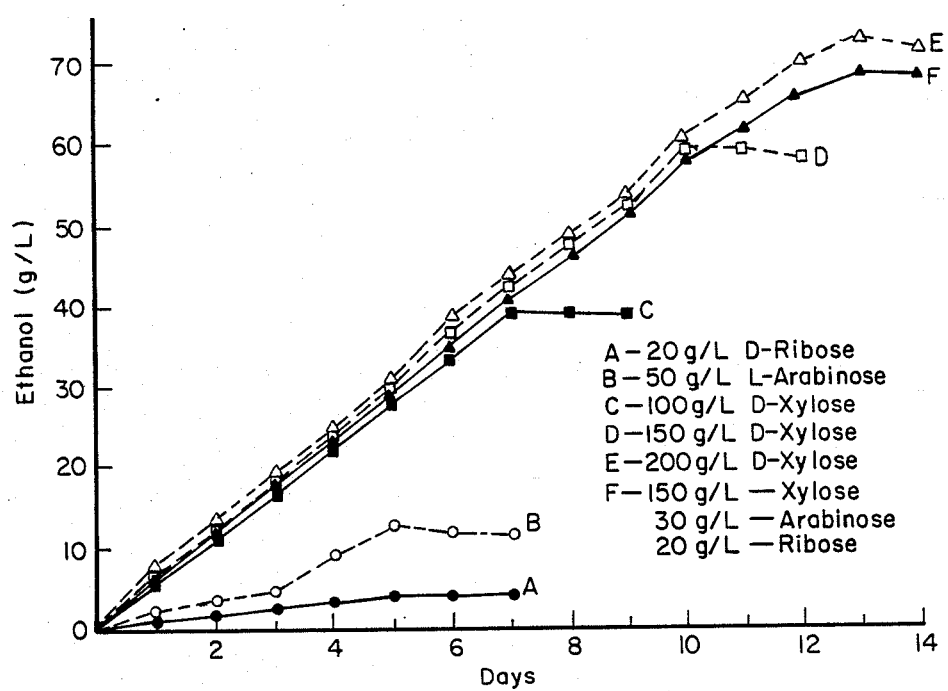
FIG. 1 is a graph depicting ethanol production from various pentoses using Paecilomyces sp.

The present invention is a process which utilizes a species of fungi to ferment a wide variety of sugar hydrolysates of both cellulose and hemicellulose. While previously known processes have shown capabilities of fermenting one or perhaps two of such sugar compositions, the essence and significant aspect of the present invention is that this process produces high yields of ethanol from a wide variety of both five-carbon and six carbon sugars derived from cellulose and hemicellulose. More particularly, the present invention ferments disaccharides such as sucrose maltose, lactose and cellobiose (but excluding melibiose and trehalose) polysaccharides such as starch pentoses such as xylose, ribose and arabinose, and hexoses such as glucose, fructose sorbose, mannose and galactose. Thus, high yields of ethanol can be produced from the bulk of the derivative by-products of cellulose and hemicellulose, thereby providing a highly economic process for producing ethanol.

Specifically, the present invention is a process using the fungus Paecilomyces sp. NF1 to produce ethanol by fermentation. The solution to be fermented may include a mixture of the cellulose hydrolysates D-cellobiose and D-glucose sugar solutions of D-xylose L-arabinose D-ribose, mannose and D-galactose derived from hemicellulose, as well as starch. It is envisioned that any combinations of the above as well as other related sugars may be fermented using the process of the present invention.

A species of the genus Paecilomyces was isolated from a soil sample and maintained on a potato dextrose agar plate. This specific fungal strain was biologically pure and is indentified as Paecilomyces sp. NF1. A sample of this strain as deposited on Aug. 6, 1985 with the culture collection of American Type Culture Collection, and is available to the public under ATCC No. 20766.

The culture medium used for fermentation in the present process can be any known culturing composition with suitable nitrogen sources mineral supplements vitamins, and carbon sources. These carbon sources may include pentoses (D-xyiose, L-arabinose, and D-ribose), hexoses (D-glucose, D-galactose, and mannose), disaccharides (D-cellobiose), and polysaccharides (starch). Samples of the culture medium were inoculated with the Paecilomyces sp. NF1 and allowed to ferment to produce ethanol. The ethanol was measured using standard gas chromatography techniques.

More specifically the inocula were prepared by transferring a loopful of the subject microorganism from the agar plate to 300 ml. Erlenmeyer flasks each containing 100 ml. of the culture medium. The specific composition of the culture medium used in the Examples provided below included 1.5 g. Yeast extract (DIFCO or SIGMA), 1.0 g. $KH_2PO_4$, 1.5 g of $KNO_3$, 0.5 g. NaCl, 0.5 g. $MgSO_4.7H_2O$, 0.1 g. $CaCl_2$, and 1.5 of the fermentable carbon substrate material. The initial inocula for the ethanol Production can be performed by either light or heavy cell density, i.e., less or greater than 6 g/l dry mycelial weight. The fungal cells can be mobilized in an alginate gel or any other desired form of stationary media. It should also be noted that any size and type (batch or continuous) of fermentation technique that is well know in the art may be utilized, and the present invention is not to be limited to the small flask, batch fermentation technique illustrated above.

The oxygen tension for the fermentation process may also vary widely. The oxygen tension can be either microaerophilic for batch fermentation, or the inoculated substrate may be sparged with a small amount of air in continuous fermentation techniques. Moreover, anaerobic fermentation may also be used. The technique will depend on the initial cell density, the substrate concentration, and the incubation condition of the inoculum.

The pH of the fermentation media can range from a pH of 2.2 to a pH of 7.0. Table I illustrates the effect of pH on ethanol production by Paecilomyces sp. NF1. These particular fermentations were carried out in anaerobic tubes at 30° C. and contained 20 g/l of xylose as the carbon source.

TABLE 1

| Initial pH | Ethanol g/l |
|---|---|
| 1.5 | 0 |
| 2.2 | 7.584–8.201 |
| 3.0 | 7.971–8.360 |
| 4.0 | 7.510–7.725 |
| 5.0 | 7.683–8.103 |
| 6.0 | 7.740–8.010 |
| 7.0 | 7.140–7.823 |

The temperature of the fermentation process of the present invention can also vary considerably from about 20° C. to about 42° C. However, the preferred range is about 30° C. to 37° C.

As indicated above, the fungal species Paecilomyces sp. NF1 of the present invention has been found capable of fermenting a wide variety of sugars. Table II outlines quantitative ethanol production by the Paecilomyces sp. NF1 fungal species utilizing a variety of different sugars as the carbon source in the above-described culture medium.

TABLE II

| Sugar | Ethanol g/l |
|---|---|
| D-Galactose | 7.692 |
| D-Glucose | 7.223 |
| Cellobiose | 7.760 |
| L-Arabinose | 4.433 |

TABLE II-continued

| Sugar | Ethanol g/l |
| --- | --- |
| Lactose | 4.255 |
| Fructose | 6.827 |
| Mannose | 6.186 |
| Maltose | 6.316 |
| Starch | 6.152 |
| D-Xylose | 5.910 |

As Table II shows, xylose, cellabiose, and glucose are all readily fermentable to substantial amounts of ethanol. Moreover, other sugars found in smaller amounts as hydrolysate by-products of cellulose and hemicellulose are also readily fermentable to ethanol. To assist in further characterizing the *Paecilomyces sp.* NF1 organism, Table III outlines the general fermentability of various carbon compounds by this microorganism with ethanol as the main fermentation product.

TABLE III

| D-Glucose | + | Melibiose | − |
| --- | --- | --- | --- |
| D-Galactose | + | Trehalose | − |
| Fructose | + | Lactose | + |
| L-sorbose | + | Starch | + |
| Mannose | + | D-xylose | + |
| Salicin | + | L-arabinose | + |
| α-methyl D-glucose | − | Xylitol | − |
| Sucrose | + | D-ribose | + |
| Maltose | + | D-cellobiose | + |

Examples of more specific fermentations using the process of the present invention are illustrated in the Examples provided below.

EXAMPLE I

Hemicellulose hydrolysates consist mainly of pentoses and hexoses, and especially xylose. To date, no yeast and only very few fungi have been found which are capable of fermenting D-ribose and L-arabinose to ethanol directly, and the fungi which have been found produce only low yields. However, it was found that *Paecilomyces sp.* NF1 was able to ferment approximately 50 g/l L-arabinose and 20 g/l of D-ribose to produce, respectively, about 12.6 g/l and 4.0 g/l ethanol. FIG. 1 illustrates these particular fermentations as well as the fermentation of various amounts of D-xylose ranging from 100–200 g/l. As can be seen from FIG. 1, in 13 days, 200 g/l of D-xylose can be fermented to yield about 74 g/l ethanol. Moreover, a mixture containing about 150 g/l D-xylose, 30 g/l L-arabinose, and 20 g/l D-ribose produced about 68 g/l of ethanol in 13–14 days. In these particular runs and in all the runs of Examples I-VII, the initial cell density was 6 g/l of the *Paecilomyces sp.* NF1 in the specific culture medium previously described, and the pH was about 5.0 with the fermentation being performed using anaerobic tubes at 30° C. and 150 RPM agitation.

EXAMPLE II

Figure 2:
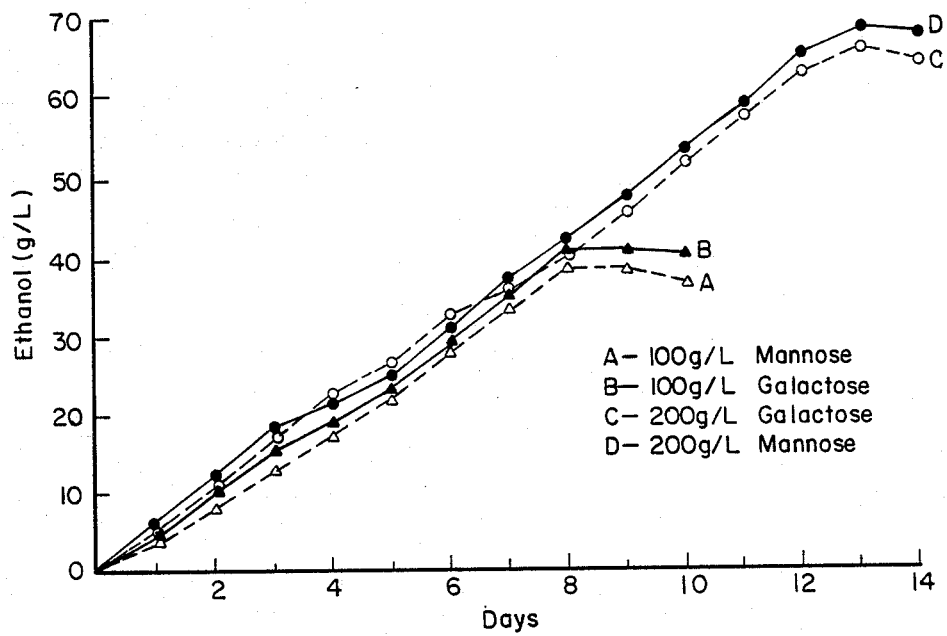
FIG. 2 is a graph illustrating ethanol production from various hexoses using Paecilomyces sp.

Two minor hydrolysate components of hemicellulose include the hexoses mannose and D-galactose. Referring to FIG. 2, it was found that the *Paecilomyces sp.* NF1 of the present invention fermented 200 g/l of each of these sugars to about 66 and 69 g/l, respectively, of ethanol. Thus, Examples I and II show that the major hydrolysate by-product constituents of hemicellulose are all readily convertible in high yields to ethanol by use of the process of the present invention. This is particularly true in the fermentation of xylose, which is very important, since xylose is by far the largest constituent of hemicellulose and, as previously indicated, has been one of the most difficult to ferment to ethanol on an economic basis.

EXAMPLE III

As previously indicated, the major hydrolysate by-product components when cellulose is hydrolyzed consist of cellobiose and glucose. Thus, D-glucose and D-cellobiose, along with D-xylose from hemicellulose, comprise the three most important and abundant renewable hydrolysates of any plant biomass. D-glucose can be readily fermented by virtually any type of fermenting microorganism. The fungus *Paecilomyces sp.* NF1 can readily ferment 100 g/l of D-glucose to produce about 40 g/l or more ethanol. Cellobiose fermentation, however, has proven difficult in the past especially when xylose fermentation is also desired.

Figure 3:
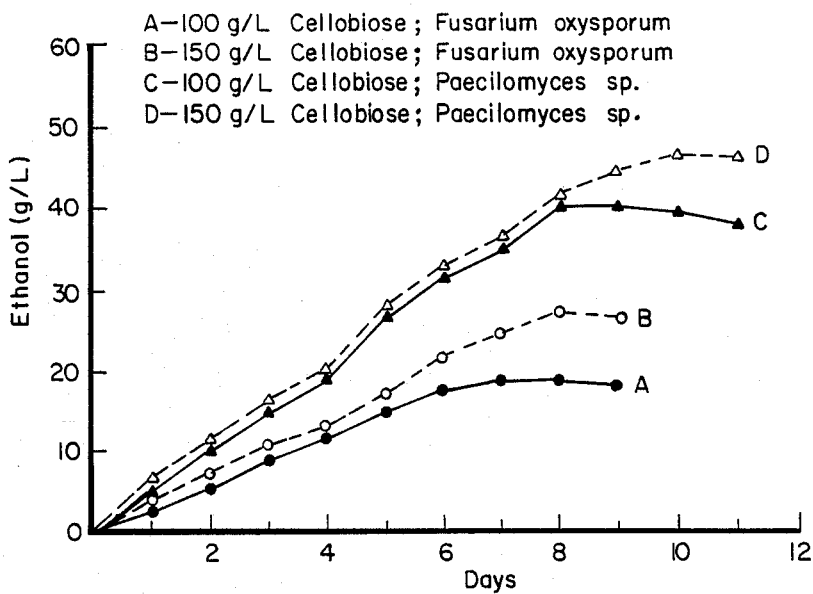
FIG. 3 is a graph illustrating ethanol production from cellobiose using Paecilomyces sp.

In the previously discussed prior art xylose fermenting yeasts, only the yeast *Kluveromyces cellobiovorus* of U.S. Pat. No. 4,472,501 can also ferment D-cellobiose in addition to the xylose. However, when the D-cellobiose substrate amounts to more than about 50 g/l, ethanol production is inhibited. Another prior art xylose fermenting fungus, *Fusarium oxysporum*, is also able to produce ethanol from D-cellobiose. However, the ethanol production from cellobiose is only about half the amount produced by the *Paecilomyces sp.* NF1 of the present invention. This is more clearly illustrated in FIG. 3 wherein cellobiose is fermented by both the *Paecilomyces sp.* NF1 and by *Fusarium oxysporum* ANL 372181.

EXAMPLE IV

Figure 4:
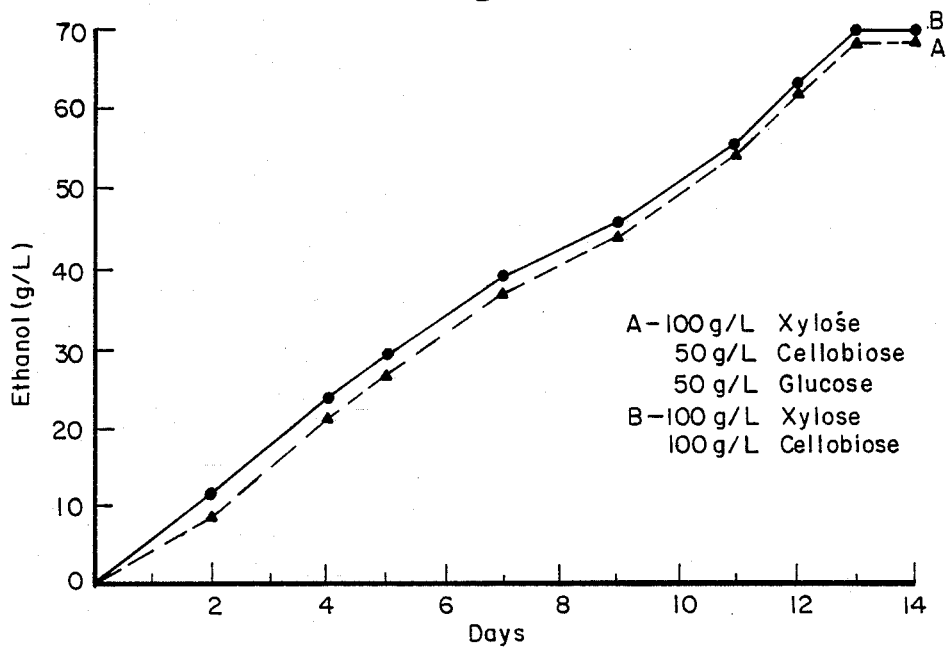
FIG. 4 is a graph illustrating ethanol production from a sugar solution containing xylose, cellobiose and glucose using Paecilomyces sp.

If a microorganism can ferment both D-cellobiose and D-xylose, it will reduce the end-product inhibition of cellulase during enzymatic hydrolysis of cellulose and thus enhance ethanol production. In this example, two different mixtures were fermented using the process of the present invention. One of the mixtures contained 50 g/l of D-glucose, 50 g/l of D-cellobiose, and 100 g/l of D-xylose as the carbon source. The other mixture contained 100 g/l of both D-cellobiose and D-xylose as the carbon source. As previously indicated under Example I, the initial cell density of the *Paecilomyces sp.* NF1 was 6 g/l, the pH was about 5.0, and fermentation was performed using anaerobic tubes at 30° C. and 150 RPM agitation. FIG. 4 illustrates the results of this Example. As can be seen from FIG. 4, about 68 g/l ethanol was produced by the first mixture and 69 g/l ethanol was produced by the second mixture. In contrast with prior art processes, ethanol production was substantially greater. For example, the *Kluveromyces cellobiovorus* can produce only about 12 g/l of ethanol from a solution containing 20 g/l D-glucose, 5 g/l D-cellobiose and 16 g/l D-xylose.

EXAMPLE V

Figure 5:
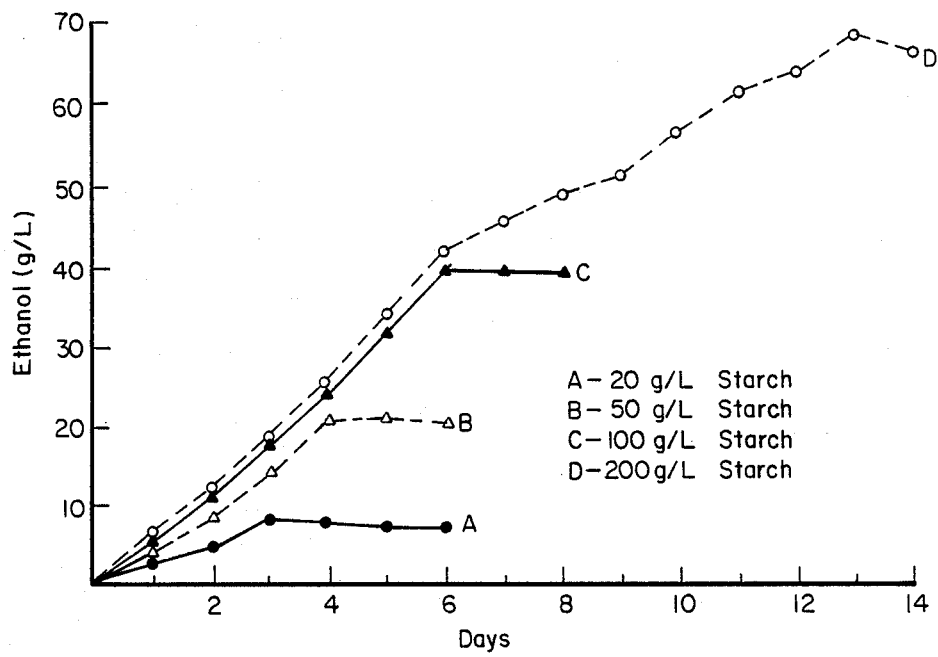
FIG. 5 is a graph illustrating ethanol production from starch using Paecilomyces sp.

In addition to cellulose and hemicellulose and the sugar hydrolysate by-products thereof, starch is a substantial storage product which is abundant in some plants. Thus, starch can be present in considerable amounts in plant biomass materials and in the hydrolysis by-products thereof. FIG. 5 illustrates the fermentation of starch using the process and fungus of the present invention. As can be seen from FIG. 5, starch can be readily fermented directly to ethanol utilizing the process of the present invention. Moreover, this can be done in conjunction with xylose fermentation as well as cellobiose fermentation. To date there is no other known yeast or fungi which is capable of fermenting all three of these substances, let alone fermenting them with the yields achievable by the present invention.

EXAMPLE VI

Hemicellulose hydrolysates were prepared by acid hydrolysis of wheat straw and wood chips. The hydrolysates had about 3 percent total sugars containing mostly 2.1% D-xylose, 0.46% D-glucose, 0.3% D-arabinose, and 0.16% D-galactose. They also contained about 0.22% acidic acid and 0.45% furfural. These hemicellulose hydrolysates were then subjected to the fermentation process of the present invention using *Paecilomyces sp.* NF1 and produced about 12.5 g/l ethanol.

EXAMPLE VII

The *Paecilomyces sp.* NF1 of the present invention was used in the simultaneous saccharification and fermentation of cellulose using 10% cellulose and the enzyme cellulase for enzymatic hydrolysis. The cellulose was Sigma Cell Type 50 and Solka-Flock CBW 200 NF, and the cellulase was NOVO SP 122. This mixture of cellulose and cellulase was subjected to the fermentation process of the present invention and produced about 40 g/l ethanol.

As can be seen from the above, the fermentation process of the present invention utilizing the fungus *Paecilomyces sp.* NF1 is capable of fermenting a wide variety of sugar compositions to ethanol. Most importantly, the major 5-carbon and 6 carbon sugar components of cellulose and hemicellulose, those being xylose, cellobiose, and glucose, are all readily fermentable to produce large yields of ethanol. Moreover, other sugar components such as hexoses and pentoses which are present in more minor amounts in plant biomass, are also readily convertible to ethanol using the process of the present invention. Thus, the vast majority of the material in plant biomass is directly fermentable to ethanol using the process of the present invention.

As a result of the above, this process is capable of providing large amounts of ethanol economically and from an almost unlimited supply of source material. The present invention thus provides a highly economic and useful process for fuel production. In addition, the hemicellulose components of plant biomass do not need to be separated prior to hydrolysis and fermentation of the by-products thereof. Thus, the fungus of the present invention can be used to ferment any sort of sugar mixture to produce ethanol thereby providing a much more economic process in terms of yield, the amount of time required to produce the ethanol, and the substrate materials which may be utilized.

The foregoing is considered as illustrative only of the principles of the invention. Further, since numerous modifications and changes will readily occur to those skilled in the art, it is not desired to limit the invention to the exact construction and operation shown and described, and accordingly all suitable modifications and equivalents may be resorted to within the scope of the invention as defined by the claims which follow.

The embodiments of the invention in which an exclusive property or privilege is claimed are defined as follows:

1. A process for producing ethanol from plant biomass comprising:

forming a substrate from said biomass, said substrate including hydrolysates of cellulose and hemicellulose;

selecting and isolating a species of the fungus *Paecilomyces sp.* NF1 which species has the ability to ferment both cellobiose and xylose to ethanol;

inoculating said substrate with said selected fungus;

fermenting said inoculated substrate under conditions favorable for cell viability and conversion of hydrolysates to ethanol; and recovering the ethanol from said substrate.

2. The process as claimed in claim 1, wherein the step of fermenting said substrate is carried out at a temperature ranging from about 20°-42° C.

3. The process as claimed in claim 2, wherein said temperature range comprises 30°-37° C.

4. The process as claimed in claim 1, wherein the pH of said inoculated substrate is maintained at about 2.2-7.0 during fermentation thereof.

5. The process as claimed in claim 1, wherein said biomass includes cellulose and hemicellulose, and wherein said substrate is formed by saccharification of said cellulose and hemicellulose.

6. The process as claimed in claim 5, wherein said saccharification step comprises acid hydrolysis.

7. The process as claimed in claim 5, wherein said saccharification step comprises enzymatic hydrolysis.

8. A process for producing ethanol from a substrate comprising:

forming a substrate selected from the group consisting of pentoses, hexoses, the disaccharides including sucrose, maltose, cellobiose and lactose, polysaccharides, and mixtures thereof;

inoculating said substrate with a species of the fungus *Paecilomyces sp.* NF1 species has the ability to ferment one or more of said, substrate components to ethanol;

fermenting said inoculated substrate under conditions favorable for cell viability and production of ethanol; and recovering the ethanol from said fermented substrate.

9. The process as claimed in claim 8, wherein the fermentation of said inoculated substrate is carried out at a temperature ranging from about 20°-42° C.

10. The process as claimed in claim 8, wherein the pH of the inoculated substrate is about 2.2-7.0 during fermentation thereof.

11. The process as claimed in claim 8, wherein said pentoses are selected from the group consisting of D-xylose, D-ribose, L-arabinose, and mixtures thereof.

12. The process as claimed in claim 8, wherein said hexoses are selected from the group consisting of D-glucose, mannose, D-galactose, fructose, sorbose, and mixtures thereof.

13. The process as claimed in claim 8, wherein said disaccharide is selected from the group consisting of D-cellobiose, sucrose, maltose, lactose, and mixtures thereof.

14. The process as claimed in claim 8, wherein said polysaccharide comprises starch.

15. The process as claimed in claim 8, wherein said substrate comprises a mixture of at least xylose, glucose and cellobiose.

16. The process as claimed in claim 8, wherein said pentoses and hexoses are hydrolysate sugars of cellulose and hemicellulose.

17. A process for producing ethanol from a substrate having a least a portion thereof selected from the group consisting of cellobiose, xylose and mixtures thereof, said process comprising the steps of:

isolating a species of the filamentous fungus *Paecilomyces sp.* NF1 the ability to ferment both cellobiose and xylose to ethanol;

inoculating said substrate with the isolated fungus;

fermenting said inoculated substrate under conditions favorable for cell viability and conversion of any cellobiose and xylose present therein to ethanol; and recovering the ethanol from said fermented substrate.

18. The process as claimed in claim 17, wherein the fermentation of said inoculated substrate is carried out at a temperature of about 20°-42° C.

19. The process as claimed in claim 17, wherein the pH of the inoculated substrate is approximately 2.2-7.0 during fermentation thereof.

20. The process as claimed in claim 17, wherein said substrate portion is derived by the acid hydrolysis of cellulose and hemicellulose.

21. The process as claimed in claim 17, wherein said substrate portion is derived by the enzymatic hydrolysis of cellulose and hemicellulose.

22. The process as claimed in claim 17, wherein said substrate comprises a mixture of at least xylose, cellobiose and glucose.

23. The process as claimed in claim 17, wherein said mixture is derived by the saccharification of cellulose and hemicellulose.

24. The process as claimed in claim 17, wherein said fermentation is carried out under aerobic conditions.

25. The process as claimed in claim 17, wherein said fermentation is carried out under anaerobic conditions. of ATCC No. 20766 and which is capable of assimilating both cellobiose and xylose to produce ethanol in recoverable amounts.

26. In a process for fermenting an aqueous fermentable sugars-containing solution to ethanol, the improvement comprising innoculating said solution with a species of the fungus *Paecilomyces sp.* NF1 which ferments sugars, to ethanol, and allowing fermentation to proceed.

27. The improvement as claimed in claim 26, wherein the fermentation is allowed to proceed until fermentation of the sugars present in said solution is substantially complete.

* * * * *